United States Patent
Choi (10) Patent No.: US 7,240,865 B2
(45) Date of Patent: Jul. 10, 2007

(54) APPARATUS FOR FOOD WASTE TREATMENT

(76) Inventor: Dong-Gak Choi, #505-1302 Hyundai Apts. 124-1, Sangok-dong, Bupyeong-gu, Incheon Metropolitan City 403-785 (KR)

(\*) Notice: Subject to any disclaimer, the term of this patent is extended or adjusted under 35 U.S.C. 154(b) by 224 days.

(21) Appl. No.: 10/537,072

(22) PCT Filed: Dec. 2, 2003

(86) PCT No.: PCT/KR03/02626

§ 371 (c)(1),
(2), (4) Date: Jun. 1, 2005

(87) PCT Pub. No.: WO2004/050268

PCT Pub. Date: Jun. 17, 2004

(65) Prior Publication Data

US 2006/0037898 A1 Feb. 23, 2006

(30) Foreign Application Priority Data

| Dec. 3, 2002 | (KR) | ............... | 10-2002-0076399 |
| Sep. 5, 2003 | (KR) | ............... | 10-2003-0062189 |
| Nov. 17, 2003 | (KR) | ............... | 10-2003-0081115 |

(51) Int. Cl.
*B02C 23/36* (2006.01)
(52) U.S. Cl. ............... 241/46.014; 241/100; 241/101.2; 241/101.8; 241/290; 241/65
(58) Field of Classification Search ............... 241/65, 241/100, 101.2, 101.8, 235, 290, 46.013–46.016
See application file for complete search history.

(56) References Cited

U.S. PATENT DOCUMENTS

| 996,958 | A | * | 7/1911 | Wallick | ............... | 241/41 |
| 5,123,600 | A | * | 6/1992 | Takenaka | ............... | 241/46.013 |

FOREIGN PATENT DOCUMENTS

| EP | 0443310 A2 * | 8/1991 |
| JP | 2000-350979 | 12/2000 |
| JP | 2002-28618 | 1/2002 |
| JP | 2002-282875 | 10/2002 |
| KR | 1988-056659 | 10/1988 |
| KR | 1999-0039464 | 6/1999 |
| KR | 20-0216319 | 12/2000 |
| KR | 20-0232293 | 5/2001 |
| KR | 20-0255688 | 11/2001 |
| KR | 2002-0073011 | 9/2002 |

\* cited by examiner

*Primary Examiner*—Mark Rosenbaum
(74) *Attorney, Agent, or Firm*—Daniel P. Burke & Associates, PLLC (57) ABSTRACT

An apparatus for food waste treatment which efficiently treats sewage and odor generated from food wastes. The food waste treatment apparatus includes a body (10), a hopper (30) to put the food wastes into the body (10), a crusher (14) installed in the body (10) to crush the food wastes, an agitating container (42) having an agitator (38) therein and provided at a lower portion in the body (10) to agitate the food wastes, a sewage purifying tank (70) provided under the crusher (14) in the body (10) so as to purify sewage generated from the food wastes during a crushing operation of the crusher (14), and a drain pipe (73) extending from the sewage purifying tank (70), with a magnetic material (74) mounted on an end of the drain pipe (73) to secondarily purify the sewage drained from the sewage purifying tank (70) into a sewer pipe.

13 Claims, 7 Drawing Sheets

APPARATUS FOR FOOD WASTE TREATMENT

TECHNICAL FIELD

The present invention relates, in general, to apparatuses for food waste treatments and, more particularly, to an apparatus for food waste treatment which efficiently treats sewage and odor generated from food wastes when the food wastes generated from a home or restaurant are treated by the apparatus.

BACKGROUND ART

Recently, a variety of techniques for apparatuses for food waste treatments have been proposed, according to an increase of the interest in environmental pollution caused by the food wastes.

As an example, an apparatus for food waste treatment, in which a compressing unit compresses the food wastes to remove water from the food wastes, has been proposed, so as to reduce odor emitted from the food wastes and decrease weight of the food wastes. The above-mentioned conventional food waste treatment apparatus reduces the environmental pollution by preventing the odor from being emitted from the wet food wastes and reduces the food wastes treatment costs, because the food waste treatment apparatus removes the water from the food wastes.

However, the conventional food waste treatment apparatus is difficult to use at home due to a large size of the apparatus. Therefore, the conventional food waste treatment apparatus is problematic in that the food wastes must be treated by the apparatus after the food wastes are separately collected from the dwellings.

Recently, in an effort to overcome the problems experienced in the conventional food waste treatment apparatus having a large size, an apparatus for food waste treatment, which is designed for home use, has been proposed. However, the conventional food waste treatment apparatus for home use does not have any purifying unit which purifies sewage generated from the food wastes when the food wastes are agitated and compressed in the conventional food waste treatment apparatus. Accordingly, the conventional food waste treatment apparatus for home use is problematic in that the sewage of the food wastes is directly drained into a sewer pipe, thus contaminating an inside surface of the sewer pipe and causing water pollution.

DISCLOSURE OF THE INVENTION

Accordingly, the present invention has been made keeping in mind the above problems occurring in the prior art, and an object of the present invention is to provide an apparatus for food waste treatment which is designed For home use and efficiently treats food wastes generated from the home, thus reducing environmental pollution.

Another object of the present invention is to provide an apparatus for food waste treatment which has a purifying unit therein to purify sewage which is generated from food wastes and is drained into a sewer pipe.

A further object of the present invention is to provide an apparatus for food waste treatment which efficiently removes odor emitted from the food wastes in the food waste treatment apparatus.

In order to accomplish the above object, the present invention provides an apparatus for food waste treatment, including a body, a hopper provided at an upper portion of the body to put food wastes into the body, and a crusher installed in the body to crush the food wastes put into the body through the hopper. The crusher includes a main crushing cutter and a main feed screw. The food waste treatment apparatus further includes an agitating container having an agitator therein and provided at a lower portion in the body to agitate the food wastes which were crushed by and dropped from the crusher, and a sewage purifying tank provided under the crusher in the body, so as to purify sewage generated from the food wastes during a crushing operation of the crusher. The sewage purifying tank includes an antibacterial filter provided at an upper portion in the sewage purifying tank, and a plurality of bio-ceramic balls contained in the sewage purifying tank and photocatalytic-coated on exterior surfaces thereof. The food waste treatment apparatus further includes a drain pipe extending from the sewage purifying tank, with a magnetic material mounted on an end of the drain pipe to secondarily purify the sewage drained from the sewage purifying tank into a sewer pipe.

The food waste treatment apparatus may further include a photocatalytic filter provided in the body to remove odor emitted from the food wastes when the food wastes are agitated by the agitator. The photocatalytic filter includes a pair of carbon ball containing blocks to contain a plurality of nano-carbon balls therein and respectively provided at inlet and outlet sides of the photocatalytic filter, a plurality of titanium dioxide blocks each having a plurality of pores, and a plurality of ultraviolet lamps arranged between the pair of carbon ball containing blocks such that the plurality of titanium dioxide blocks and the plurality of ultraviolet lamps are alternately arranged between the pair of carbon ball containing blocks.

The food waste treatment apparatus may further include a catalytic oxidation filter provided at a predetermined position in the body to remove the odor emitted from the food wastes when the food wastes are agitated by the agitator. The catalytic oxidation filter includes a catalytic oxidation block and a heater to maintain a desired temperature of the catalytic oxidation block.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Reference should now be made to the drawings, in which the same reference numerals are used throughout the different drawings to designate the same or similar components.

Figure 1:
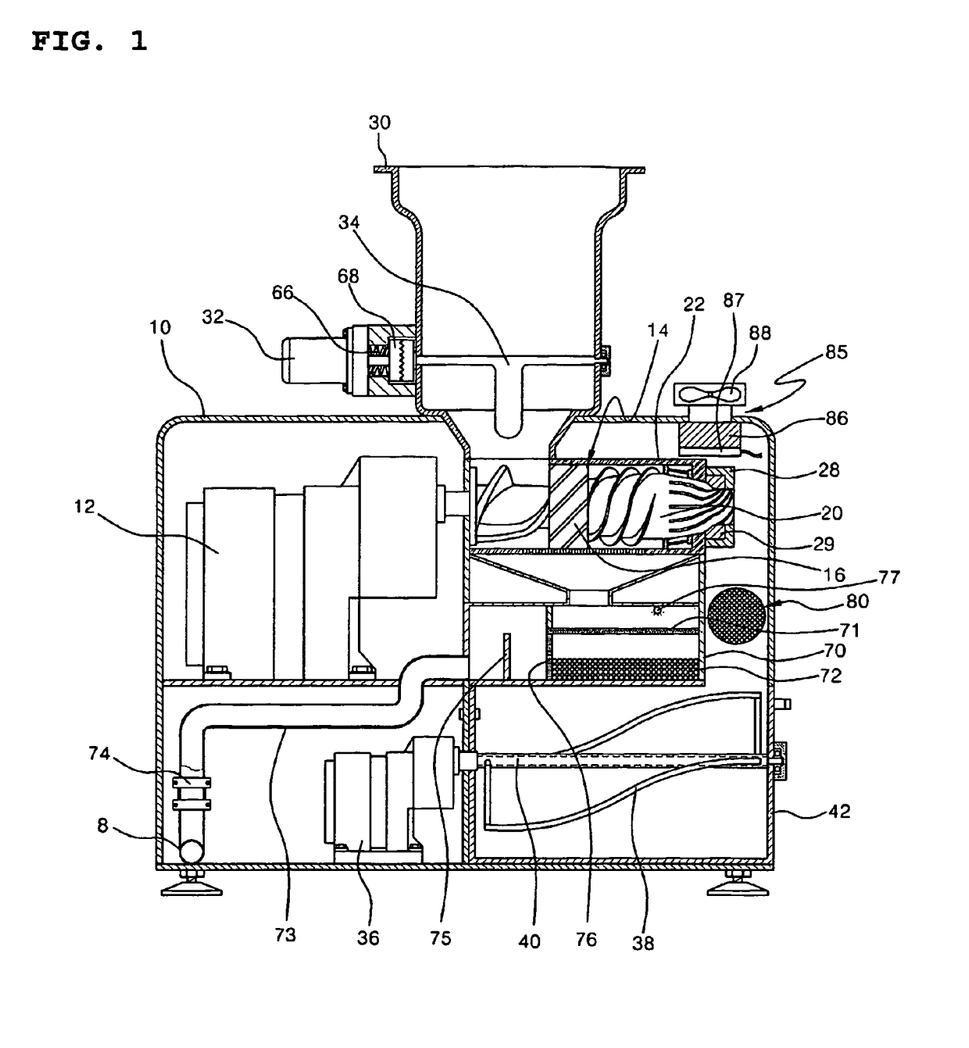
FIG. 1 is a sectional view showing an internal construction of an apparatus for food waste treatment, according to a first embodiment of the present invention.
Figure 2:
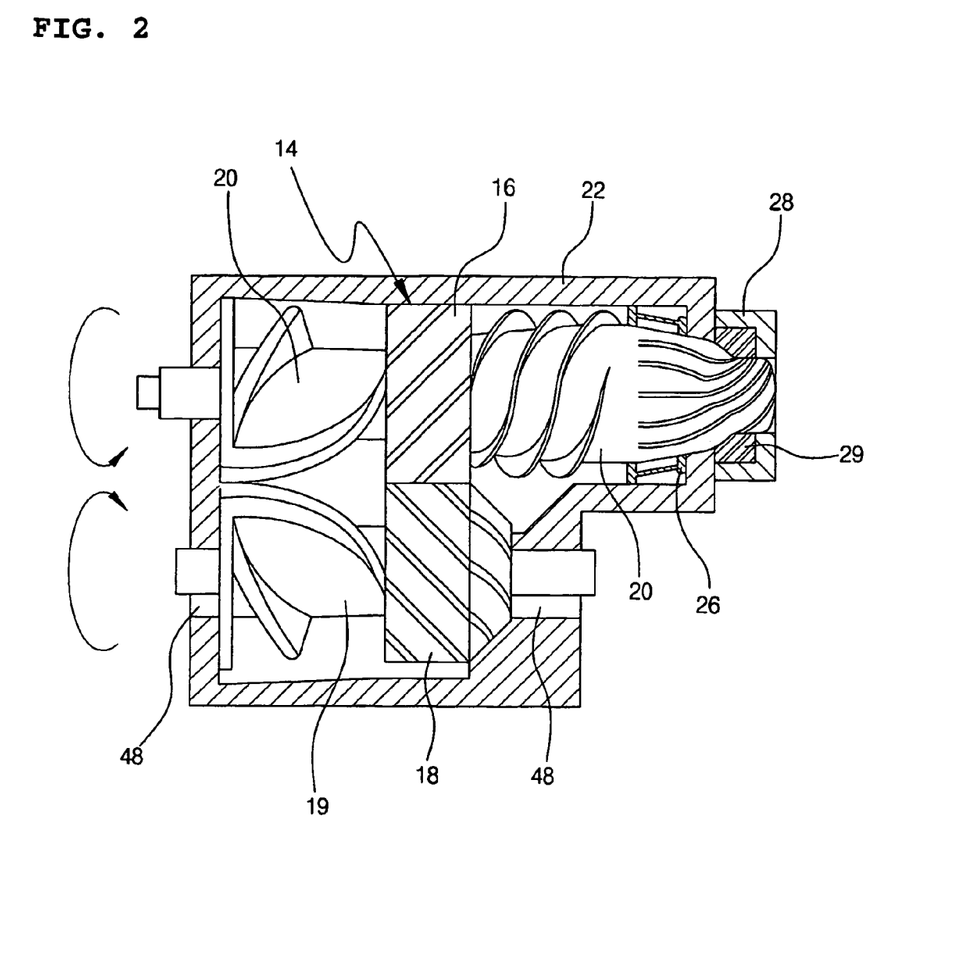
FIG. 2 is a top sectional view of a crusher of the food waste treatment apparatus of FIG. 1.
Figure 3:
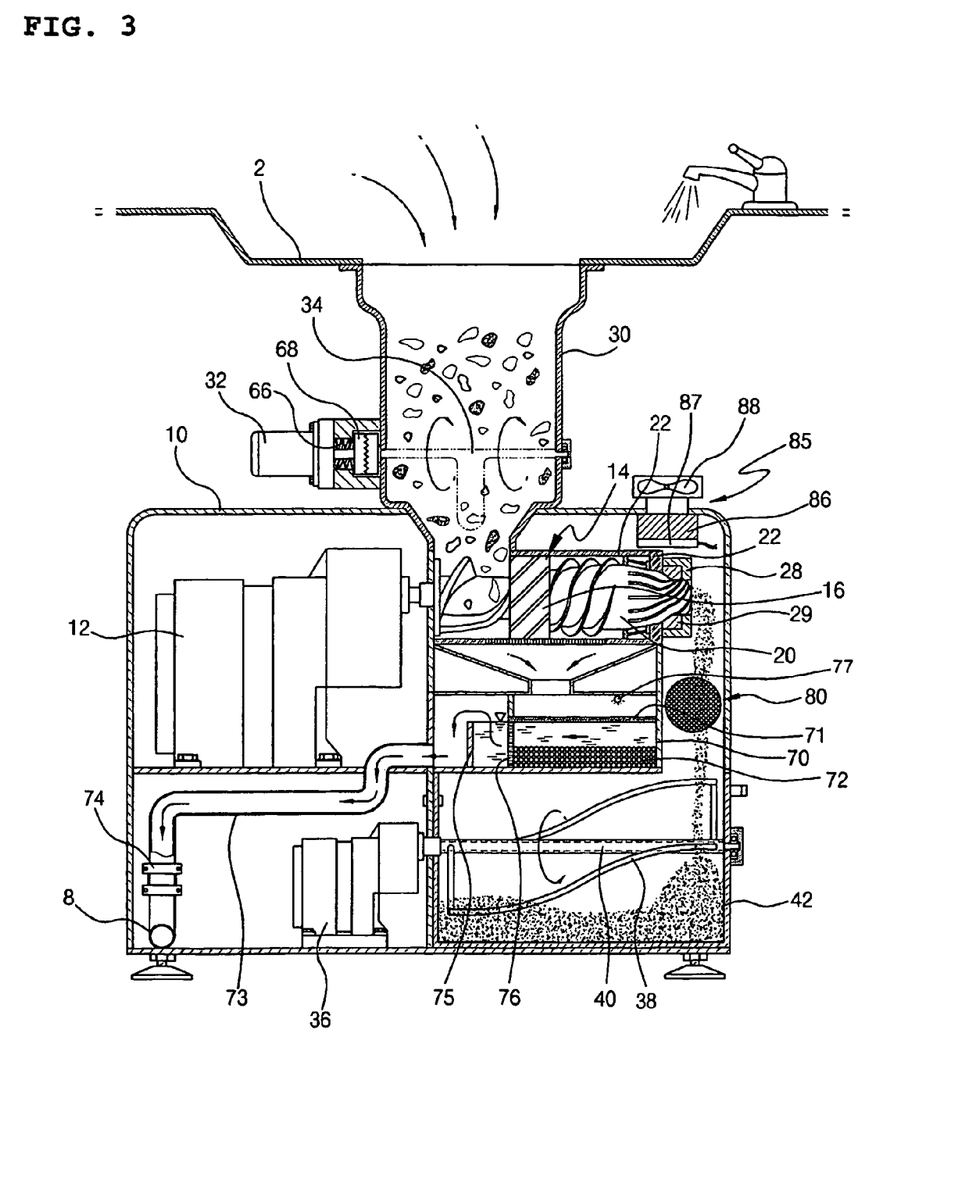
FIG. 3 is a sectional view showing an operation of the food waste treatment apparatus of FIG. 1.
Figure 4:
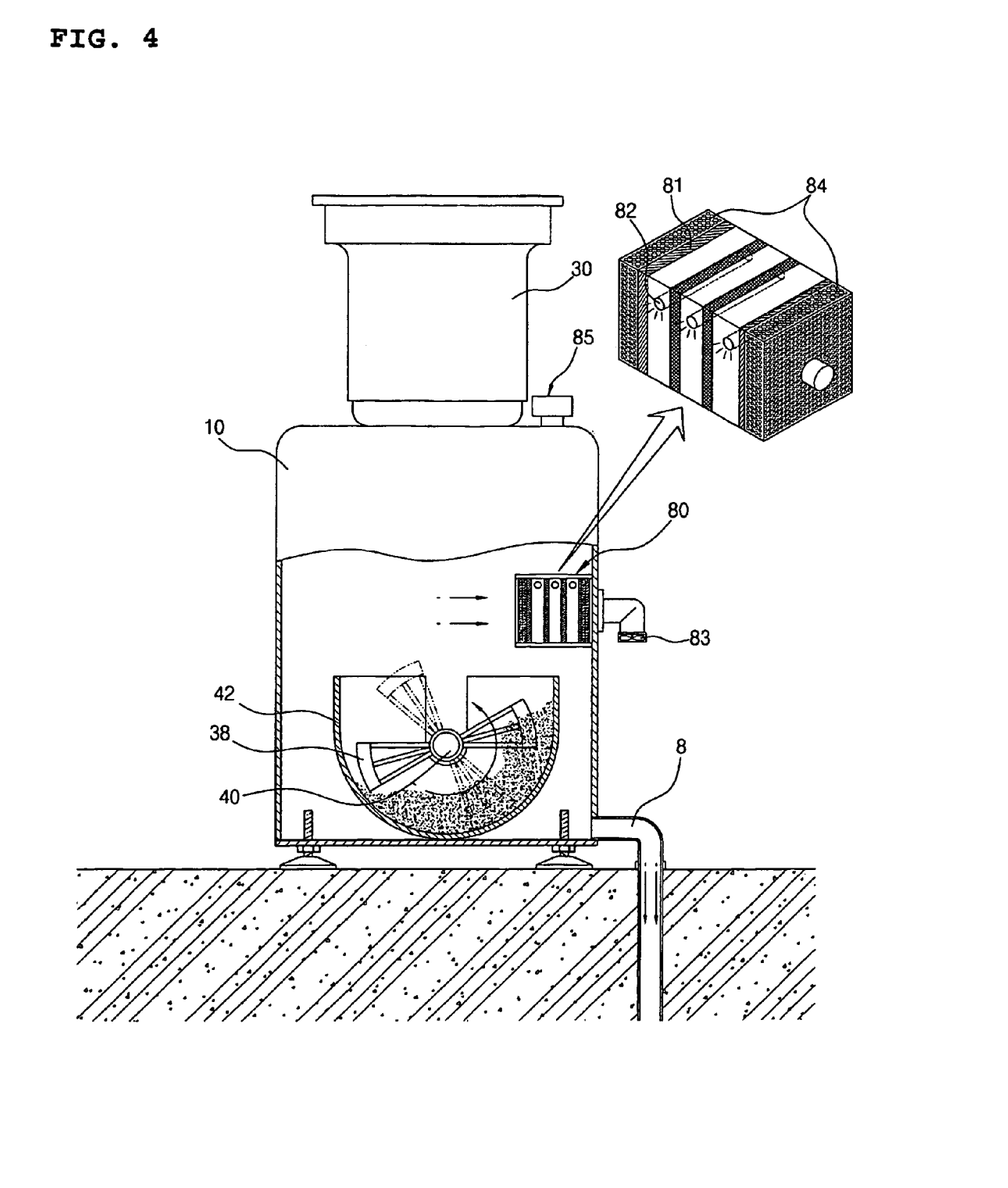
FIG. 4 is a partially broken sectional view showing an operation of an agitator in an agitating container of the food waste treatment apparatus of FIG. 1.
Figure 5:
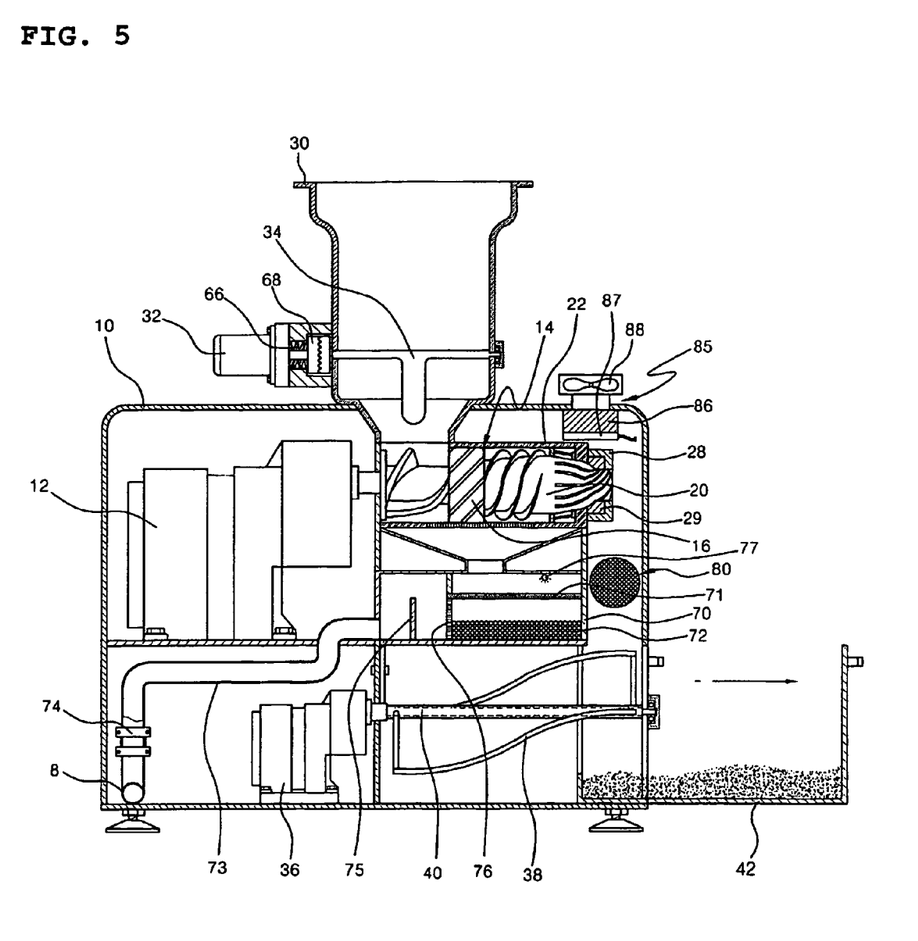
FIG. 5 is a sectional view showing an opening motion of the agitating container of the food waste treatment apparatus of FIG. 1.

FIG. 1 is a sectional view showing an internal construction of an apparatus for food waste treatment, according to a first embodiment of the present invention. FIG. 2 is a top sectional view of a crusher 14 of the food waste treatment apparatus of FIG. 1. FIG. 3 is a sectional view showing an operation of the food waste treatment apparatus of FIG. 1. FIG. 4 is a partially broken sectional view showing an operation of an agitator 38 in an agitating container 42 of the food waste treatment apparatus of FIG. 1. FIG. 5 is a sectional view showing an opening motion of the agitating container 42 of the food waste treatment apparatus of FIG. 1.

As shown in FIGS. 1 to 5, the apparatus for food waste treatment of the first embodiment of the present invention includes a body 10, a hopper 30 which is provided at an upper portion of the body 10 to put food wastes into the body 10, the crusher 14 which is housed in a crusher housing 22 installed in the body 10 to crush the food wastes which were put into the body 10 through the hopper 30, and a crushing motor 12 which is installed at a predetermined position in the body 10 to rotate the crusher 14. The food waste treatment apparatus further includes the agitating container 42 which has an agitator 38 therein and is provided at a lower portion in the body 10 to agitate the food wastes which were crushed by and dropped from the crusher 14. The agitator 38 is rotated by an agitating motor 36 which is installed at a predetermined position in the body 10. The agitating container 42 further has a rod-type heater 40 therein to dry the food wastes when the food wastes are agitated by the agitator 38. The rod-type heater 40 has a role as a rotating shaft of the agitator 38.

The hopper 30 includes a push bar 34 therein at a lower portion thereof to forcibly put the food wastes into the crusher 14 in the body 10. The push bar 34 is rotated by a push motor 32 which is mounted on an external surface of the lower portion of the sidewall of the hopper 30. The push motor 32 is a reversible motor. The push motor 32 has a spring 66 and a clutch 68 therein to temporarily interrupt the transmission of a rotating force, which is transmitted from the push motor 32 to the push bar 34, by reversibly rotating the push motor 32 in case of an emergency, such as an overload.

As shown in FIG. 2, the crusher 14 includes a main crushing cutter 16, with a main feed screw 20 integrated with the main crushing cutter 16 into a single structure. A compressing silicon pad 29 and a compressing cap 28 are mounted on an external surface of the crusher housing 22 around a first end of the main feed screw 20 which is projected to the outside of the crusher housing 22, so as to finely crush the food wastes passing through a water eliminator 26 which is provided at the first end of the main feed screw 20 in the crusher housing 22. A sub-crushing cutter 18 is provided in the crusher housing 22 to engage with the main crushing cutter 16. The sub-crushing cutter 18 is tapered at a first side thereof and has a rotating shaft which is held at both ends thereof in guide holes 48 which are provided on both sidewalls of tile crusher housing 22, such that the sub-crushing cutter 18 moves within a predetermined range provided by the guide holes 48.

In the meantime, the food waste treatment apparatus further includes a sewage purifying tank 70 under the crusher 14 in the body 10, so as to purify sewage generated from the food wastes during a crushing operation of the crusher 14. The sewage purifying tank 70 includes an antibacterial filter 71 which is provided at an upper portion in the sewage purifying tank 70, and a plurality of bio-ceramic balls 72 which are contained in the sewage purifying tank 70 and photocatalytic-coated on exterior surfaces thereof. The food waste treatment apparatus further includes a drain pipe 73 which extends from the sewage purifying tank 70. The drain pipe 73 has a magnetic material 74 at an end thereof to secondarily purify the sewage drained from the sewage purifying tank 70 into a sewer pipe. The magnetic material 74 of the drain pipe 73 preferably comprises a rare-earth permanent magnet. The sewage purifying tank 70 further includes a backflow prevention plate 75 therein to maintain a level of the sewage in the sewage purifying tank 70 to a predetermined height, so that odor, emitted from the sewage drained into the drain pipe 73, is prevented from flowing in a reverse direction from an inlet of the drain pipe 73. The backflow prevention plate 75 is made of a tourmaline ceramic which radiates a large quantity of far infrared rays and anions. In the drawings, The reference numeral 76 denotes a screen which prevents losses of the bio-ceramic balls 72, and 77 denotes a ultraviolet (UV) lamp which activates the photocatalytic-reactions of the bio-ceramic balls 72.

As shown in FIG. 4, the food waste treatment apparatus further includes a photocatalytic filter 80 and a catalytic oxidation filter 85 at predetermined positions in the body, so as to remove odor emitted from the food wastes when the food wastes are agitated by the agitator 38 in the agitating container 42. The photocatalytic filter 80 has a plurality of titanium dioxide blocks 81 each having a plurality of pores, and a plurality of ultraviolet lamps 82, such as ultraviolet (UV) fluorescent lamps. The plurality of titanium dioxide blocks 81 and the plurality of ultraviolet lamps 82 are alternately arranged. The odor, emitted from the food wastes when the food wastes are agitated by the agitator 38, is captured by the photocatalytic filter 80 and is discharged to the outside by a first discharging fan 83 which is provided at a predetermined position of the external surface of the body 10. The catalytic oxidation filter 85 includes a catalytic oxidation block 86 and a heater 87 to maintain a temperature of the catalytic oxidation block 86 at about 200° C. which is the temperature to efficiently accomplish an effect of the catalytic oxidation. The odor, emitted from the food wastes when the food wastes are agitated by the agitator 38, is captured by the catalytic oxidation block 86 and is discharged by a second discharging fan 88 which is provided above the catalytic oxidation filter 85.

Particularly, each of the titanium dioxide blocks 81 comprises anatase-type photocatalytic titanium dioxide ($TiO_2$) nano-particles, of which the average particle size is 20 nm. Each of the titanium dioxide blocks 81 includes materials having specific functions, such as antibacterial, anti-fungal, and deodorant functions, etc. The photocatalytic filter 80 further has a pair of carbon ball containing blocks 84 which contain a plurality of nano-carbon balls therein and respectively provided at inlet and outlet sides of the photocatalytic filter 80, so as to efficiently remove the odor.

Next, the operation and effect of the food waste treatment apparatus of the first embodiment of the present invention will be described herein below.

The food wastes and water are put into the hopper 30 through a sink 2 which is provided above the hopper 30. At this time, in case that large-sized food wastes are put into the hopper 30, the large-sized food wastes are forcibly put into the crusher 14 by the push bar 34 which is rotated by the push motor 32, so that the large-sized food wastes are easily put into the crusher 14. The push motor 32 rotates slowly. If a user mistakenly or carelessly puts his/her hand is put into the hopper 30 during a rotating motion of the push bar 34, the push bar 34 is temporally stopped by interrupting the transmission of the rotating force from the push motor 32 to the push bar 34 by actions of the spring 66 and the clutch 68 of the push motor 32, thus preventing safety hazards during the operation of the apparatus.

Thereafter, the food wastes, put into the crusher 14, are crushed by the feed screw 20 and the main cutter 16 of the crusher 14 which are simultaneously rotated by a rotating force transmitted from the crushing motor 12, and is transferred to a first side of the crusher 14. At this time, the sub-crushing cutter 18, which engages with the main crushing cutter 16, is rotated in a direction opposite to the rotating direction of the main crushing cutter 16. Furthermore, the sub-crushing cutter 18 moves within the predetermined range provided by the guide holes 48 of the crusher housing 22, according to the amount of the food wastes crushed by the crusher 14, so as to reduce loads imposed on the main crushing cutter 16, the sub-crushing cutter 18 and the crushing motor 12 when the overload is applied to the crusher 14.

The sub-crushing cutter 18 is tapered at the first side thereof, so that the crusher 14 reduces a pressure which is generated at a first side of the main feed screw 20 when the crushed food wastes are fed to the first side of the main feed screw 20, thus smoothly transferring the food wastes to the first side of the crusher 14.

That is, in the crusher 14, the food wastes are fed by the main feed screw 20 and a sub-feed screw 19 into the main crushing cutter 16 and the sub-crushing cutter 18 which engage with each other to be respectively rotated, so that the food wastes are crushed into the small pieces.

At this time, the food wastes in the crusher 14 are transferred along and crushed by blades of the main and sub crushing cutters 16 and 18 while the blades are respectively rotated around the main and sub crushing cutters 16 and 18 and engage with each other. During the above-mentioned crushing operation, a predetermined amount of water contained in the food wastes is removed from the food wastes.

Sequentially, the food wastes, having crushed by the crusher 14, are transferred along the first side of the main feed screw 20 to the water eliminator 26, and a predetermined amount of water is removed from the food wastes by a predetermined pressure applied to the food wastes which are continuously fed into the water eliminator 26.

Thereafter, the food wastes, having processed by the water eliminator 26, are fed along spiral grooves formed on an external surface of the first end of the main feed screw 20 into the compressing silicon pad 29 and the compressing cap 28, so that the food wastes are finely crushed by the compressing silicon pad 29 and is dropped through the compressing cap 28 into the agitating container 42 which is provided at the lower portion of the body 10.

In the agitating container 42, the food wastes are agitated by the agitator 38 which is rotated by a rotating force transmitted from the agitating motor 36, and is rapidly dried by the rod-type heater 40 in the agitating container 42, thus preventing the food wastes from decaying.

In the agitating container 42, microbial chips are added to be agitated with the food wastes by the agitator 38, so as to ferment the food wastes. A sensor (not shown) is provided in the agitating container 42 to monitor an amount of the food wastes contained in the agitating container 42. When the amount of the food wastes in the agitating container 42 is more than a predetermined reference level, the sensor outputs a signal to a control panel (not shown) to alarm to the user, so that the user collects the fermented food wastes from the agitating container 42.

As shown in FIG. 5, because the agitating container 42 is installed in the body 10 in to move a sliding manner, the user simply collects the food wastes from the agitating container 42. The fermented food wastes, agitated in the agitating container 42 with the microbial chips, may be used as farmyard manure or feed stuff for cattle.

In the meantime, the sewage, generated from the food wastes during the crushing operation of the crusher 14, is guided along an inclined surface of a lower portion of the crusher housing 22 and flows into the sewage purifying tank 70. Thereafter, the sewage in the sewage purifying tank 70 is primarily purified by passing through the antibacterial filter 71 and is secondarily purified by passing through the plurality of bio-ceramic balls 72 which are contained in the sewage purifying tank 70 and are photocatalytic-coated on the exterior surfaces thereof.

The sewage, generated from the food wastes during the crushing operation of the crusher 14, contains oils, plural bacteria and various kinds of microbes. The number of microbes contained in the sewage reduces while the sewage passes through the antibacterial filter 71. In addition, organic compounds contained in the sewage are dissolved by a bactericidal action and a far-infrared radiating action of the bio-ceramic balls 72 and the backflow prevention plate 75 which is made of the tourmaline ceramic.

The sewage in the sewage purifying tank 70 is thirdly purified by the rare-earth permanent magnetic material 74 which is mounted on the end of the drain pipe 73, while passing through the drain pipe 73. At this time, water of the sewage is ion-activated by a magnetic field of the magnetic material 74, so that chroma, turbidity and deodorization of the sewage are improved.

The purified sewage is thereafter drained through a sewer hole 8 into the sewer pipe. Even though the sewage is drained into the sewer pipe, impurities are prevented from being deposited in the sewer pipe, and existing rust and scale are removed. Furthermore, the purified sewage is kept in a magnetized state during seven to ten days, thus preventing pollution of odor and virus caused by the sewer pipe.

In the meantime, the odor, emitted from the food wastes when the food wastes are processed in the food waste treatment apparatus, is removed by the photocatalytic filter 80 and the catalytic oxidation filter 85 in the body 10. In the photocatalytic filter 80 which is provided at a side position in the body 10, the plurality of titanium dioxide blocks 81 are spaced apart from each other at predetermined intervals. The plurality of ultraviolet lamps 82 are respectively arranged in the gaps defined between the plurality of titanium dioxide blocks 81. When ultraviolet radiated rays from each of the ultraviolet lamps 82 are radiated on each of the titanium dioxide blocks 81, a reducing power of a hydrogen peroxide ($H_2O_2$) and a oxidizing power of a hydroxyl group are generated on a surface of each of the titanium dioxide blocks 81, so that a variety of contaminants and harmful components of the odor are dissolved and removed. Thereafter, the odor is discharged by the first discharging fan 83 to the outside of the body 10. In the catalytic oxidation filter 85, the catalytic molecules of the catalytic oxidation block 86 are activated by the heater 87, so that the odor in the body 10 is removed when the air passes through the catalytic oxidation filter 85. Thereafter, the odorless air is discharged by the second discharging fan 88 to the outside of the body 10.

Figure 6:
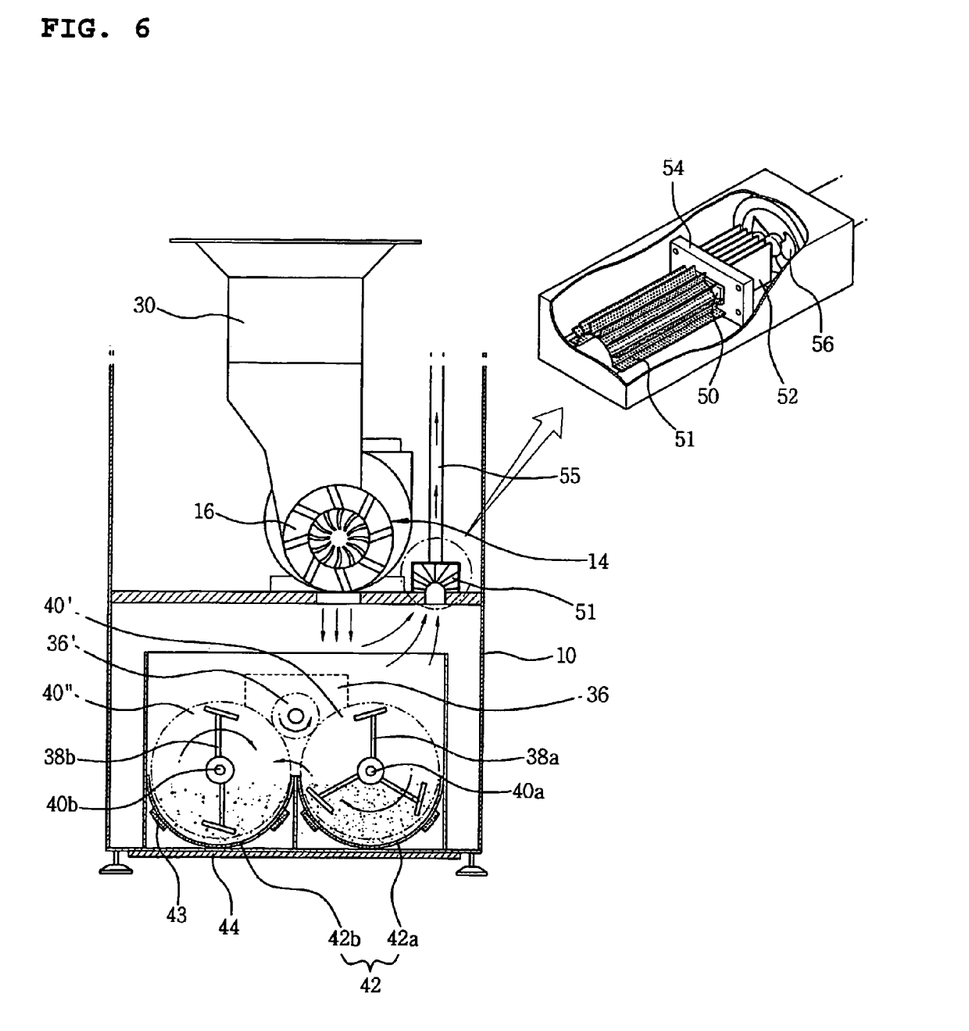
FIG. 6 is a sectional view of an apparatus for food waste treatment, according to a second embodiment of the present invention.
Figure 7:
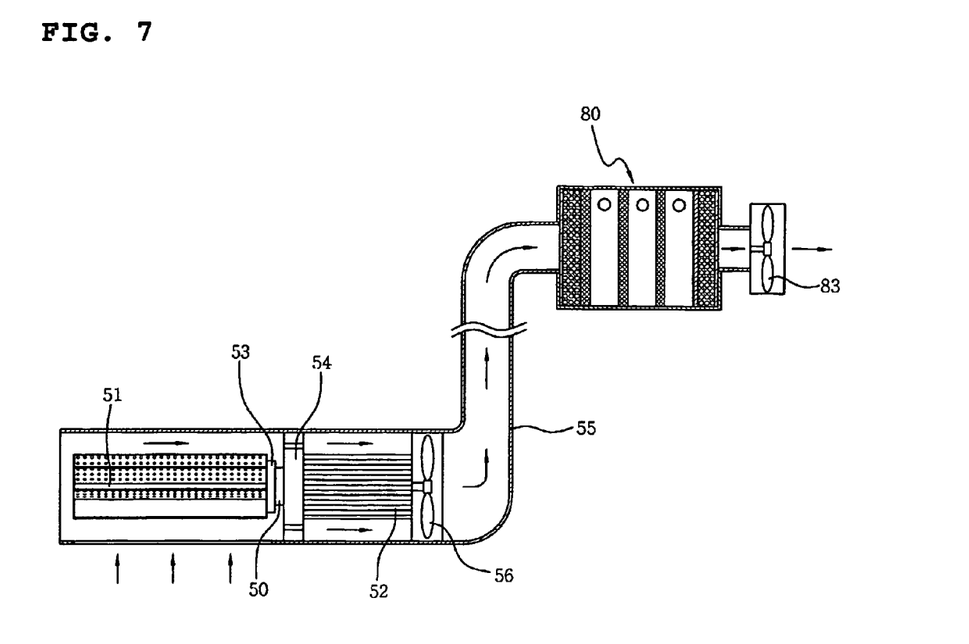
FIG. 7 is a sectional view showing an air flow channel of the food waste treatment apparatus of FIG. 6, in which currents of air of high temperature flowing in the air flow channel are shown.

FIGS. 6 and 7 are views of an apparatus for food waste treatment, according to a second embodiment of the present invention.

As shown in FIGS. 6 and 7, in the food waste treatment apparatus of the second embodiment of the present invention, the crusher 14 is placed in the body 10 to be offset from a bottom part of the hopper 30, so as to easily crush the food wastes which are put into the crusher 14 through the hopper 30. Two first and second agitating containers 42*a* and 42*b* are provided under the crusher 14 in the body 10. First and second agitators 38*a* and 38*b* are rotated by the rotating force which is transmitted from the agitating motor 36 thereto via first and second agitating gears 40' and 40" which are respectively provided at ends of first and second rotating shaft 40*a* and 40*b* of the first and second agitators 38*a* and 38*b*. Because a motor gear 36' of the agitating motor 36 is mounted between the first and second agitating gears 40' and 40" to engage with each other, the first and second agitating gears 40' and 40" are rotated in opposite rotating directions. At this time, an electrical solenoid valve may be additionally provided between the motor gear 36' and the second agitating gear 40" to selectively rotate the second agitator 38*b*.

A positive temperature coefficient (PTC) thermister heating element 43, which is a sensor-type heater of which the quantity of heat varies in response to an environmental temperature, is attached on a lower surface of a bottom of each of the first and second agitating containers 42*a* and 42*b*, without using the rod-type heater 40 used as the rotating shaft of the agitator 38, different from the food waste treatment apparatus of the first embodiment of the present invention. Accordingly, the first and second agitating containers 42*a* and 42*b* dry the food wastes therein using instantaneous heat of the PTC thermister heating element 43 without putting the microbial chips into the first and second agitating containers 42*a* and 42*b*. Selectively, a carbon fiber heater 44 may be attached on a lower surface of a bottom of the body 10, so as to maintain the agitating temperatures of the first and second agitating containers 42*a* and 42*b* in the range of 40° C. to 60° C. when the microbial chips are put into the first and second agitating containers 42*a* and 42*b*.

As a condensing means to condense vapor in the air of a high temperature, a thermoelectric module 50 using a direct current is provided above the first and second agitating containers 42*a* and 42*b*, with a cooling fin 51 and a heating fin 52 coupled to a cooling side and a heating side of the thermoelectric module 50, respectively. The cooling fin 51 has a plurality of pores for a flow of the air. Particularly, in the food waste treatment apparatus of the second embodiment of the present invention, the thermoelectric module 50 accomplishes a peltier effect, so that the thermoelectric module 50 rapidly changes the operation of the apparatus between cold and hot modes, thus efficiently dehumidifying the air.

In the drawings, the reference numeral 53 denotes a cooling block, 54 denotes a radiating block, 55 denotes an air guide channel which guides the inside air of the body 10 into the photocatalytic filter 80 before discharging the air to the outside of the body 10, and 56 denotes a blower fan.

The operation of the food waste treatment apparatus according to the second embodiment of the present invention having the above-mentioned construction will be described herein below. The food wastes, having crushed by the crusher 14, are dropped into the first agitating container 42*a* and is agitated by the first agitator 38*a* while the first agitating gear 40', which is provided at the end of a first rotating shaft 40*a* of the first agitator 38*a*, is rotated by the rotating force transmitted from the agitating motor 36 thereto via the motor gear 36'.

When the food wastes fill the first agitating container 42*a*, a predetermined amount of food wastes is transferred into the second agitating container 42*b* and is secondarily agitated by the second agitator 38*b* in the second agitating container 42*b*. At this time, the food wastes are dried by the instantaneous heat of the PTC thermister heating element 43, without putting the microbial chips into the first and second agitating container 42*a* and 42*b*.

In the meantime, the air of both high temperature and humidity and the odor, which are generated from the food wastes while the food wastes are agitated and dried in the first and second agitating containers 42*a* and 42*b*, rise in the body 10, and is condensed by passing through the cooling pin 51. Thereafter, the odor is removed from the air while the air having the odor passes through the photocatalytic filter 80, and the odorless air is discharged to the outside of the body 10.

Because the cooling fin 51 is in contact with the cooling side of the thermoelectric module 50, the cooling fin 51 constantly maintains a low-temperature state. Therefore, the cooling fin 5 easily condenses the vapor in the air of the high temperature. The heating fin 52 of the thermoelectric module 50 executes a heat radiating operation.

The food waste treatment apparatus of the present invention efficiently crushes and dries the food wastes, and efficiently purifies the sewage generated from the food wastes during the crushing operation of the crusher 14. In addition, the food waste treatment apparatus of the present invention efficiently removes the odor, emitted from the food wastes while the food wastes are processed in the body 10, by the photocatalytic effect and the catalytic oxidation effect provided in the food waste treatment apparatus, thus preventing air pollution and water pollution.

INDUSTRIAL APPLICABILITY

As described above, the present invention provides an apparatus for food waste treatment which efficiently reduces a volume of food wastes generated from home or restaurant by crushing and drying the food wastes. In the food waste treatment apparatus of the present invention, the food wastes are agitated in an agitating container together with microbial chips, so that the food wastes processed by the food waste treatment apparatus may be preferably used as farmyard manure or feed stuff for cattle.

Furthermore, the food waste treatment apparatus of the present invention efficiently purifies sewage, generated from the food wastes during a crushing operation of a crusher and drained into a sewer pipe, by providing an antibacterial effect and by executing an ultraviolet radiating operation, thus reducing pollution of water in a sewer pipe and preventing odor and virus caused by the sewer pipe.

In addition, the food waste treatment apparatus of the present invention efficiently removes the odor, emitted from the food wastes while the food wastes are processed in the food waste treatment apparatus, by a photocatalytic effect and a catalytic oxidation effect provided in the food waste treatment apparatus, thus reducing the odor contained in the air discharged from the food waste treatment apparatus and preventing air pollution.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An apparatus for food waste treatment, comprising:
    a body;
    a hopper provided at an upper portion of the body to put food wastes into the body;
    a crusher installed in the body to crush the food wastes put into the body through the hopper, the crusher comprising a main crushing cutter and a main feed screw;
    an agitating container having an agitator therein and provided at a lower portion in the body to agitate the food wastes which were crushed by and dropped from the crusher;
    a sewage purifying tank provided under the crusher in the body, so as to purify sewage generated from the food wastes during a crushing operation of the crusher, the sewage purifying tank including;
        an antibacterial filter provided at an upper portion in the sewage purifying tank; and
        a plurality of bio-ceramic balls contained in the sewage purifying tank and photocatalytic-coated on exterior surfaces thereof; and
    a drain pipe extending from the sewage purifying tank, with a magnetic material mounted on an end of the drain pipe to secondarily purify the sewage drained from the sewage purifying tank into a sewer pipe.

2. The apparatus according to claim 1, further comprising a photocatalytic filter provided in the body to remove odor emitted from the food wastes when the food wastes are agitated by the agitator, the photocatalytic filter comprising:
    a pair of carbon ball containing blocks to contain a plurality of nanocarbon balls therein and respectively provided at inlet and outlet sides of the photocatalytic filter;
    a plurality of titanium dioxide blocks each having a plurality of pores; and
    a plurality of ultraviolet lamps arranged between the pair of carbon ball containing blocks such that the plurality of titanium dioxide blocks and the plurality of ultraviolet lamps are alternately arranged between the pair of carbon ball containing blocks.

3. An apparatus according to claim 2 further comprising a catalytic oxidation filter provided at a predetermined position in the body to remove the odor emitted from the food wastes when the food wastes are agitated by the agitator, the catalytic oxidation filter comprising a catalytic oxidation block and a heater to maintain a desired temperature of the catalytic oxidation block.

4. An apparatus according to claim 2 further comprising:
    an air flow channel provided above the agitating container to guide air from the agitating container into the photocatalytic filter;
    a cooling fin mounted on the air flow channel to condense vapor in the air of a high temperature guided from the agitating container into the photocatalytic filter through the air flow channel; and
    a thermoelectric module mounted on an end of the cooling fin such that a cooling side of the thermoelectric module is in contact with the end of the cooling fin.

5. The apparatus according to claim 1, further comprising a catalytic oxidation filter provided at a predetermined position in the body to remove the odor emitted from the food wastes when the food wastes are agitated by the agitator, the catalytic oxidation filter comprising a catalytic oxidation block and a heater to maintain a desired temperature of the catalytic oxidation block.

6. The apparatus according to claim 1, wherein the crusher which is installed in the body is housed in a crusher housing, with a sub-crushing cutter provided in the crusher housing to engage with the main crushing cutter, the sub-crushing cutter having a rotating shaft which is held at both ends thereof in guide holes provided on both sidewalls of the crusher housing, such that the sub-crushing cutter moves within a predetermined range provided by the guide holes.

7. The apparatus according to claim 1, wherein the agitating container further comprises a rod-type heater therein to dry the food wastes when the food wastes are agitated by the agitator, the rod-type heater having a role as a rotating shaft of the agitator.

8. The apparatus according to claim 1, wherein the hopper further comprises a push bar therein to forcibly put the food wastes into the crusher in the body.

9. The apparatus according to claim 6, wherein the sub-crushing cutter of the crusher is tapered at a first side thereof, with a sub-feed screw integrally provided at a second side of the sub-crushing cutter.

10. The apparatus according to claim 1, wherein the crusher is placed in the body to be offset from a bottom part of the hopper, and the agitating container comprises a plurality of containers.

11. An apparatus according to claim 10 further comprising a positive temperature coefficient (PTC) thermister heating element or a carbon fiber heater provided under the agitating container to heat the agitating container.

12. The apparatus according to claim 1, further comprising a positive temperature coefficient (PTC) thermister heating element or a carbon fiber heater provided under the agitating container to heat the agitating container.

13. The apparatus according to claim 1, further comprising:
    an air flow channel provided above the agitating container to guide air from the agitating container into the photocatalytic filter;
    a cooling fin mounted on the air flow channel to condense vapor in the air of a high temperature guided from the agitating container into the photocatalytic filter through the air flow channel; and
    a thermoelectric module mounted on an end of the cooling fin such that a cooling side of the thermoelectric module is in contact with the end of the cooling fin.

* * * * *